United States Patent [19]
Hager

[11] Patent Number: 5,868,908
[45] Date of Patent: Feb. 9, 1999

[54] SEPARATION OF INORGANIC SALTS FROM DIMETHYL SULFOXIDE

[75] Inventor: James L. Hager, Eau Claire County, Wis.

[73] Assignee: WRR Environmental Services Co., Inc., Eau Claire, Wis.

[21] Appl. No.: 926,003

[22] Filed: Sep. 9, 1997

[51] Int. Cl.⁶ .............................. B01D 1/22; B01D 3/10; B01D 3/34
[52] U.S. Cl. ................... 203/68; 203/89; 203/91; 159/49; 159/DIG. 16; 159/47.3
[58] Field of Search .................. 203/89, 91, 68, 203/14, 57, 69, 70; 159/49, DIG. 16, 47.3; 208/348; 568/27; 210/774

[56] References Cited

U.S. PATENT DOCUMENTS

| | | | |
|---|---|---|---|
| 3,939,036 | 2/1976 | Erwin | 159/47.1 |
| 4,094,748 | 6/1978 | Schumacher | 203/88 |
| 5,190,619 | 3/1993 | Berg et al. | 203/51 |
| 5,599,979 | 2/1997 | Berg | 562/606 |

*Primary Examiner*—Virginia Manoharan
*Attorney, Agent, or Firm*—Tipton L. Randall

[57] ABSTRACT

A process for separating inorganic salts from a solution of dimethyl sulfoxide, water and salts including feeding the solution plus a hydrocarbon based oil to a vacuum thin film evaporator. The DMSO and water are vaporized and condensed outside the evaporator for reuse or further purification. The salt and oil exit the evaporator as a liquid phase slurry. Water is added to the slurry to dissolve the salt and produce an aqueous phase and an oil phase which are separated. The oil phase is recycled to the thin film evaporator portion of the process.

15 Claims, 2 Drawing Sheets

SEPARATION OF INORGANIC SALTS FROM DIMETHYL SULFOXIDE

FIELD OF THE INVENTION

This invention relates to a process for separation of inorganic salts from dimethyl sulfoxide, and more particularly for the separation of inorganic salts from a solution of salts in dimethyl sulfoxide and water.

BACKGROUND OF THE INVENTION

Dimethyl sulfoxide, also known in the industry as DMSO, is a dipolar aprotic solvent which is useful for dissolving both ionic and covalent compounds. DMSO dissolves ionic salts, such as sodium chloride or potassium bromide, as well as many nonionic compounds of low molecular weight. When using DMSO as a solvent for both inorganic salts and organic compounds in a single operation, the standard method for separating the organic compound from the DMSO and salts is to add water to the solution. The DMSO and salts enter the water phase, while the organic material forms a second phase which can be easily separated by physical means.

The resulting DMSO/inorganic salt/water phase can present a difficult disposal problem. In addition, DMSO is a fairly expensive solvent and thus, recovery would provide an economic incentive as well as overcome the problem of disposal.

In other situations, DMSO may be contaminated with inorganic salts alone. Again, purification of the DMSO by removal of the soluble inorganic salts may be necessary.

Berg, in U.S. Pat. No. 5,599,979 discloses the use of extractive distillation, which separates two compounds with similar boiling points by adding a higher boiling substance, to separate formic acid from acetic acid.

In U.S. Pat. No. 5,190,619 Berg et al. disclose the separation of 3-methyl-2-butanone from formic acid by extractive distillation with DMSO plus an additional compound. None of these references address the separation of inorganic salts from DMSO or DMSO/water/salt solutions.

Attempts to separate and recover DMSO from solutions of DMSO/inorganic salts/water or DMSO/inorganic salts by either thin film evaporators or vacuum distillation are not successful since, at even moderately elevated temperatures, DMSO and inorganic salts can react to decompose and contaminate the DMSO. Often the reaction is sufficiently exothermic that a dangerous condition results, possibly damaging the separation apparatus and endangering the system operator. Attempts to separate inorganic salts from DMSO/water solutions at lower temperatures by vacuum fractionation also encounter difficulties where the salt becomes insoluble and sticks to the surfaces of the apparatus used in the fractionation. The insoluble salt may collect to the point of plugging pipes and heat exchange equipment.

To overcome this problem in the recovery of DMSO from the above described solvent solutions, applicant has discovered a new process for separation and recovery of DMSO.

SUMMARY OF THE INVENTION

The invention comprises a process for the separation of DMSO from inorganic salts as well as from solutions of DMSO, inorganic salts and water. The process comprises the steps of feeding a dimethyl sulfoxide, water and salt solution plus a hydrocarbon oil, in a selected proportion to the solution, to a thin film evaporator operated at reduced pressure and elevated temperature, with upper and lower outlets. Dimethyl sulfoxide and water enter a vapor phase and the salt and hydrocarbon oil remain in a liquid slurry phase.

Dimethyl sulfoxide and water as a vapor phase are removed from the upper outlet of the thin film evaporator, while salt and hydrocarbon oil as a liquid slurry phase are removed from the lower outlet of the thin film evaporator.

The vapor phase containing dimethyl sulfoxide and water is condensed to produce a liquid phase containing dimethyl sulfoxide and water suitable for reuse or further purification.

Liquid water is added to the oil and salt liquid slurry phase from the evaporator lower outlet to dissolve a substantial portion of the inorganic salt, producing an aqueous salt solution phase and a hydrocarbon oil phase.

The hydrocarbon oil phase is separated from the aqueous salt solution phase and the separated hydrocarbon oil therefrom is added to the influent dimethyl sulfoxide, water and inorganic salt solution for removal of additional inorganic salt therefrom.

In a further embodiment of the invention, the liquid dimethyl sulfoxide and water phase from the thin film evaporator is treated by fractional distillation at reduced pressure and elevated temperature, to produce an essentially pure separated dimethyl sulfoxide phase and a separated water phase with the water phase added to the separated oil and salt liquid slurry to effect the separation described above.

DESCRIPTION OF THE PREFERRED EMBODIMENTS

Figure 1:
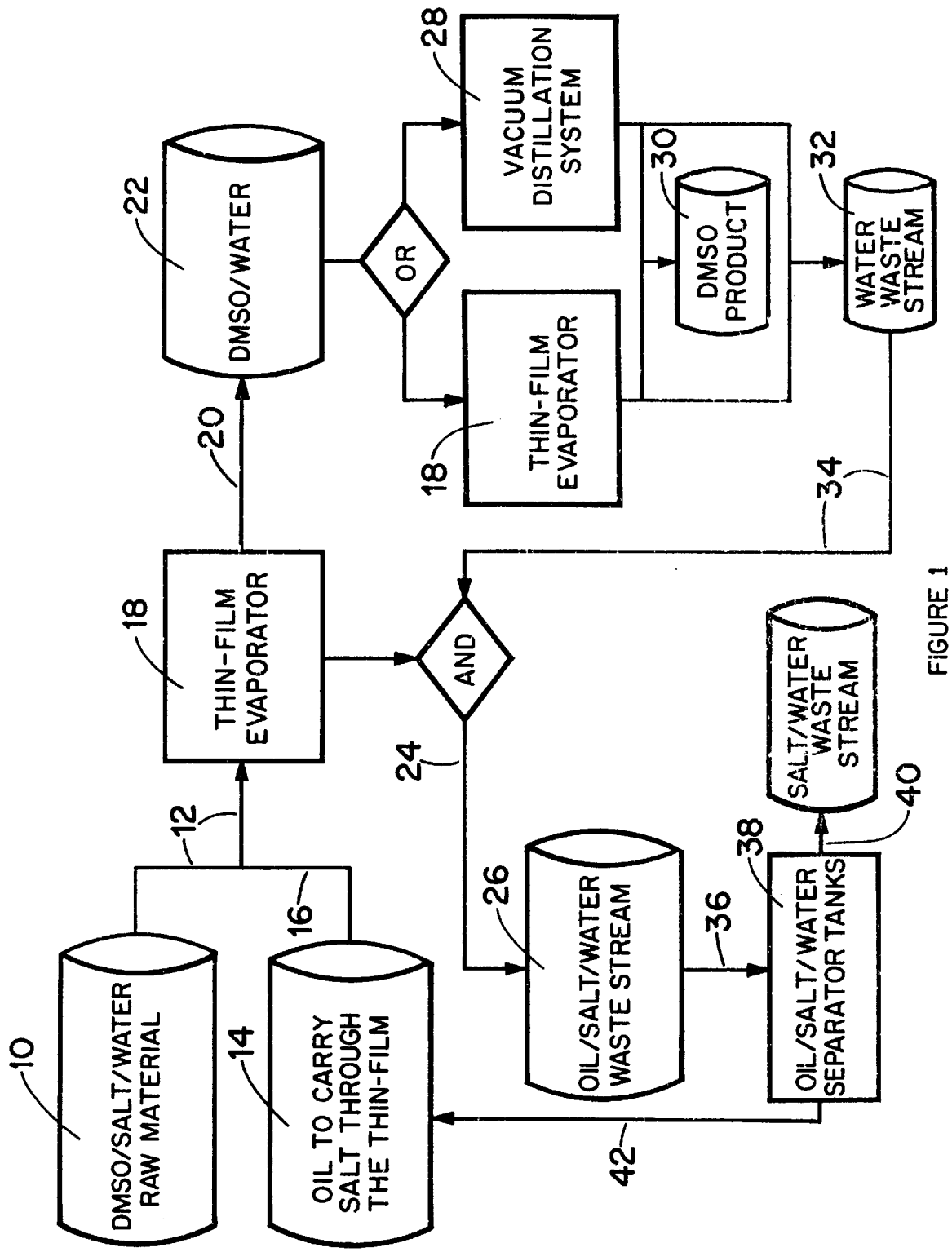
FIG. 1 is a flow diagram of the process of the instant invention.

Referring to FIG. 1, a storage tank 10 contains the raw material comprising a solution of DMSO, salt and water. The solution flows from the storage tank 10 through a conduit 12 where the solution mixes with a selected amount of a hydrocarbon based oil from an oil tank 14 connected to the conduit 12 via a conduit 16. The two phases mix and then enter a thin film evaporator unit 18 operated at reduced pressure and elevated temperature. The operating pressure of the evaporator unit is at least less than about 67.7 Kpa (20 inches of mercury) and the operating temperature is between about 160° and 182° C. (320° and 360° F.).

Within the thin film evaporator unit, the DMSO and water components are separated from the salt and oil components. The DMSO and water components are condensed and transferred via a conduit 20 to the DMSO/water storage tank 22 while the oil and salt slurry stream, carried via a conduit 24, is mixed with water to dissolve salts and then routed to a storage tank 26. The resulting DMSO/water solution in the tank 22 may be suitable for reuse in a process which generated the raw material in storage tank 10. Alternatively, the DMSO and water components may be separated by rectification using either a second thin film evaporator unit 18, or a vacuum distillation unit 28. Either system is operated at reduced pressure of at least less than about 67.7 KPa (20 inches of mercury) and temperatures between about 160° and 182° C. (320° and 360° F.). This simple separation process produces an essentially pure DMSO component stored in tank 30, and a water component stored in tank 32. The water stream from the tank 32 optionally may be employed to dissolve the insoluble salts from the oil/water slurry produced by the first thin film evaporator unit 18. Water from the storage tank 32 is routed via a conduit 34 to the conduit 24 to mix with the oil/salt slurry. The resulting oil/salt/water mixture in tank 26 flows via a conduit 36 to a separator tank 38 where phase separation is achieved. The aqueous salt water solution phase is separated and sent to disposal via a conduit 40. The separated oil phase is routed via a conduit 42 to the oil storage tank 14 for reuse in the separation process.

Figure 2:
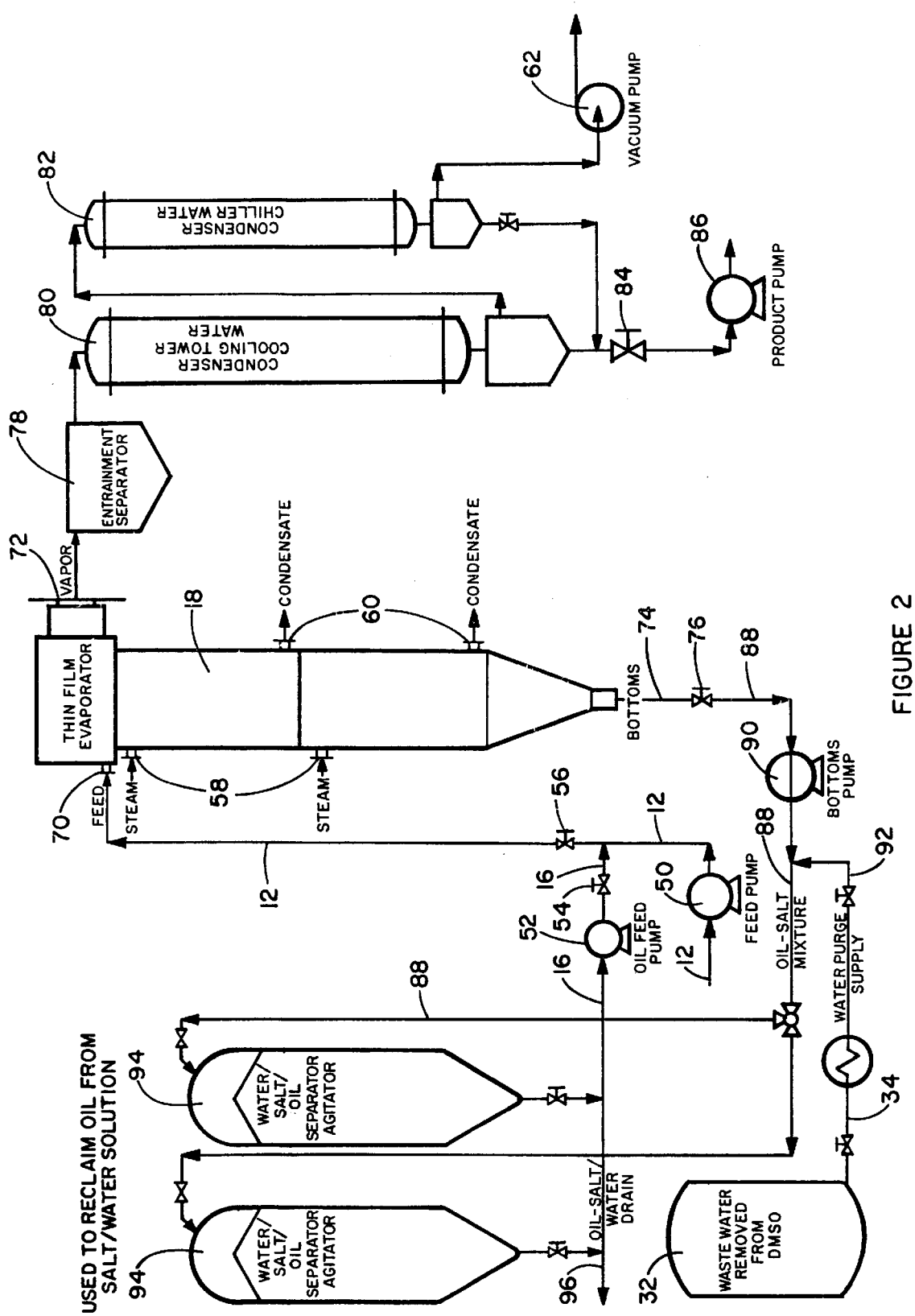
FIG. 2 is a detailed view of the thin film evaporator section of the process.

The details of the separation process are show in FIG. 2, where elements common with FIG. 1 have the same indica. Raw material containing a solution of DMSO, salt and water in a feed conduit 12 flows by means of a feed pump 50 to a thin film evaporator 18. A hydrocarbon based oil in the oil conduit 16 flows by means of an oil pump 52 to mix with the components in the feed conduit 12. The proportion of oil mixed with the feed stream is controlled by a valve 54 in the oil conduit 16, while the flow of the feed plus oil mixture to the thin film evaporator unit 18 is controlled by a valve 56 in the conduit 12, downstream of the point of introduction of the oil. The thin film evaporator unit 18 is a standard vertical conduit with concentric heating jacket. The inner conduit contains a rotating wiper blade or a similar device to spread the feed material over the surface of the inner conduit. The evaporator unit 18 is heated by introducing steam through several steam inlet ports 58 with steam condensate removed through the exit ports 60. The reduced pressure within the system is maintained by a vacuum pump 62 connected to the downstream end of the system.

The DMSO, salt, water and oil mixture from the feed conduit 12 enters the top of the thin film evaporator unit 18 via an inlet port 70, with liquid phase passing down the surface of the inner conduit. At the reduced pressure and elevated temperature of the system, DMSO and water enter the vapor phase while the salt and hydrocarbon oil remain as a liquid slurry phase, with the vapor phase exiting the evaporator via an upper vapor outlet 72, and the liquid slurry phase exiting the evaporator via a lower liquid outlet conduit 74, controlled by a valve 76.

Attempts to operate the thin film evaporator unit 18 without the hydrocarbon oil added to the raw DMSO, water and salt stream result in salt adhering to the inside of the thin film evaporator 18 and exit conduit 74. The hydrocarbon oil employed is sufficiently high boiling that it remains in the liquid phase at the conditions within the thin film evaporator 18. The hydrocarbon oil coats the interior of the inner conduit and wiper blade, as well as downstream piping and prevents the insoluble salt from adhering to these surfaces. The oil also carries along the insoluble salt to further treatment downstream. The proportion of oil added to the DMSO, water and salt solution depends on the amount of salt in the solution. Roughly about 5% to 15% by volume of oil is required for the process to operate effectively, with about 10% by volume of oil being the preferred proportion required.

The DMSO and water components in the vapor phase exit the thin film evaporator unit via an outlet 72, pass through an entrainment separator 78, and then encounter a train of condensers, including a first condenser 80 using cooling tower water, followed by a second condenser 82 using chiller water to cool and condense the vapor components. The second condenser 82 is connected to vacuum pump 62 which maintains the system reduced operating pressure. The liquid from the condensers, made up of DMSO and water, is combined and passes through a control valve 84 to a product pump 86, and the solution is pumped to the storage tank 22 for reuse or further separation.

The hydrocarbon oil and salt slurry exit the thin film evaporator via a conduit 74 controlled by a control valve 76. The slurry moves through a conduit 88 and is pumped with a pump 90 to the oil reclamation portion of the process. The oil and salt slurry in the conduit 88 is mixed with sufficient water from a conduit 92 to dissolve a substantial portion of the salt. The water may be fresh water or it may be all or a portion of the water stream separated from the DMSO/water stream originating from the thin film evaporator and subjected to rectification. The resulting mixture of oil and aqueous salt solution flows via the conduit 88 to one or more phase separation vessels 94 where the aqueous salt water phase is separated from the hydrocarbon oil phase. The aqueous salt water phase is sent to waste via a conduit 96 while the oil phase is transferred from the separator 94 to the oil storage tank 14 via a conduit 42 for reuse in the separation process.

As mentioned above, DMSO may be contaminated with inorganic salts alone and purification of the DMSO is required. In this case, a portion of water is added to the DMSO salt solution and the resulting mixture is subjected to the separation process described above.

While the invention has been particularly shown and described with reference to a preferred embodiment thereof, it will be understood by those skilled in the art that various changes in form and details may be made therein without departing from the spirit and scope of the invention.

I claim:

1. A process for separating inorganic salts from a dimethyl sulfoxide, water and salt solution comprising the steps:

a) feeding said dimethyl sulfoxide, water and inorganic salt solution and an added hydrocarbon oil, in a selected proportion to said solution, to a thin film evaporator operated at reduced pressure and elevated temperature, with upper and lower outlets, wherein said dimethyl sulfoxide and water enter a vapor phase and said salt and said hydrocarbon oil remain in a liquid slurry phase;

b) removing said dimethyl sulfoxide and said water as a vapor phase from said upper outlet of said thin film evaporator and removing said salt and said hydrocarbon oil as a liquid slurry phase from said lower outlet of said thin film evaporator;

c) condensing by cooling said vapor phase containing said dimethyl sulfoxide and water to produce a liquid phase containing dimethyl sulfoxide and water for reuse or further purification;

d) adding liquid water to said oil and salt liquid slurry phase from step b) to dissolve a substantial portion of said inorganic salt to produce an aqueous salt solution phase and a hydrocarbon oil phase; and e) separating said hydrocarbon oil phase from said aqueous salt solution phase and adding said separated hydrocarbon oil therefrom to said dimethyl sulfoxide, water and inorganic salt solution of step a) to remove additional inorganic salt therefrom.

2. A process according to claim 1 wherein said reduced pressure in the thin film evaporator of steps a) and b) is less than about 67.7 KPa, and said elevated temperature in the thin film evaporator of steps a) and b) is between about 160° C. and 182° C.

3. A process according to claim 1 wherein said selected proportion of hydrocarbon oil to said dimethyl sulfoxide, water and salt solution is between about 5 percent and 15 percent by volume of said oil to said solution.

4. A process according to claim 1 wherein said selected proportion of hydrocarbon oil to said dimethyl sulfoxide, water and salt solution is about 10 percent by volume of said oil to said solution.

5. A process according to claim 1 wherein said hydrocarbon oil added to said dimethyl sulfoxide, water and salt solution has a boiling point higher than dimethyl sulfoxide and water at the reduced pressure and elevated temperature.

6. A process for separating inorganic salts and water from a dimethyl sulfoxide, water and salt solution and recovering purified dimethyl sulfoxide comprising the steps:

a) feeding said dimethyl sulfoxide, water and inorganic salt solution and an added hydrocarbon oil, in a selected proportion to said solution, to a thin film evaporator operated at reduced pressure and elevated temperature with upper and lower outlets, wherein said dimethyl sulfoxide and water enter a vapor phase and said salt and said hydrocarbon oil remain in a liquid slurry phase;

b) removing said dimethyl sulfoxide and said water as a vapor phase from said upper outlet of said thin film evaporator and removing said salt and said hydrocarbon oil as a liquid slurry phase from said lower outlet of said thin film evaporator;

c) condensing by cooling said vapor phase containing said dimethyl sulfoxide and water to produce a liquid phase containing dimethyl sulfoxide and water;

d) separating said dimethyl sulfoxide from said water by treating said liquid phase of step c) by fractional distillation or in the thin film evaporator at reduced pressure and elevated temperature to produce a separated water phase and a separated dimethyl sulfoxide phase;

e) adding said separated water phase from step d) to said oil and salt liquid slurry phase from step b) to dissolve a substantial portion of said inorganic salt to produce and aqueous salt solution phase and a hydrocarbon oil phase; and f) separating said hydrocarbon oil phase from said aqueous salt solution phase and adding said separated hydrocarbon oil therefrom to said dimethyl sulfoxide, water and inorganic salt solution of step a) to remove additional inorganic salt therefrom.

7. A process according to claim 6 wherein said reduced pressure in the thin film evaporator of steps a), b) and d) is less than about 67.7 KPa, and said elevated temperature in the thin film evaporator of steps a), b) and d) is between about 160° C. and 182° C.

8. A process according to claim 6 wherein said selected proportion of hydrocarbon oil to said dimethyl sulfoxide, water and salt solution is between about 5 percent and 15 percent by volume of said oil to said solution.

9. A process according to claim 6 wherein said selected proportion of hydrocarbon oil to said dimethyl sulfoxide, water and salt solution is about 10 percent by volume of said oil to said solution.

10. A process according to claim 6 wherein said hydrocarbon oil added to said dimethyl sulfoxide, water and salt solution has a boiling point higher than dimethyl sulfoxide and water at the reduced pressure and elevated temperature.

11. A process for separating inorganic salts from a dimethyl sulfoxide and salt solution comprising the steps:

a) adding a selected portion of water to said dimethyl sulfoxide and salt solution to form a dimethyl sulfoxide, water and salt solution;

b) feeding said dimethyl sulfoxide, water and inorganic salt solution and an added hydrocarbon oil, in a selected proportion to said solution, to a thin film evaporator operated at reduced pressure and elevated temperature, with upper and lower outlets, wherein said dimethyl sulfoxide and water enter a vapor phase and said salt and said hydrocarbon oil remain in a liquid slurry phase;

c) removing said dimethyl sulfoxide and said water as a vapor phase from said upper outlet of said thin film evaporator and removing said salt and said hydrocarbon oil as a liquid slurry phase from said lower outlet of said thin film evaporator;

d) condensing by cooling said vapor phase containing said dimethyl sulfoxide and water to produce a liquid phase containing dimethyl sulfoxide and water for reuse or further purification;

e) adding liquid water to said oil and salt liquid slurry phase from step c) to dissolve a substantial portion of said inorganic salt to produce an aqueous salt solution phase and a hydrocarbon oil phase; and f) separating said hydrocarbon oil phase from said aqueous salt solution phase and adding said separated hydrocarbon oil therefrom to said dimethyl sulfoxide, water and inorganic salt solution of step b) to remove additional inorganic salt therefrom.

12. A process according to claim 11 wherein said reduced pressure in the thin film evaporator of steps a) and b) is less than about 67.7 KPa, and said elevated temperature in the thin film evaporator of steps a) and b) is between about 160° C. and 182° C.

13. A process according to claim 11 wherein said selected proportion of hydrocarbon oil to said dimethyl sulfoxide, water and salt solution is between about 5 percent and 15 percent by volume of said oil to said solution.

14. A process according to claim 11 wherein said selected proportion of hydrocarbon oil to said dimethyl sulfoxide, water and salt solution is about 10 percent by volume of said oil to said solution.

15. A process according to claim 11 wherein said hydrocarbon oil added to said dimethyl sulfoxide, water and salt solution has a boiling point higher than dimethyl sulfoxide and water at the reduced pressure and elevated temperature.

* * * * *